(12) United States Patent
MacLaughlan

(10) Patent No.: US 10,806,741 B2
(45) Date of Patent: Oct. 20, 2020

(54) TREATMENTS FOR FREE-LIVING AMOEBIC INFECTIONS

(71) Applicant: Todd Ewen MacLaughlan, Orlando, FL (US)

(72) Inventor: Todd Ewen MacLaughlan, Orlando, FL (US)

(73) Assignee: Profounda, Inc., Orlando, FL (US)

( * ) Notice: Subject to any disclaimer, the term of this patent is extended or adjusted under 35 U.S.C. 154(b) by 0 days.

(21) Appl. No.: 16/515,745

(22) Filed: Jul. 18, 2019

(65) Prior Publication Data

US 2020/0093842 A1   Mar. 26, 2020

Related U.S. Application Data

(60) Provisional application No. 62/735,338, filed on Sep. 24, 2018.

(51) Int. Cl.

| | |
|---|---|
| *A61K 31/661* | (2006.01) |
| *A61K 9/00* | (2006.01) |
| *A61P 33/04* | (2006.01) |
| *A61K 31/155* | (2006.01) |
| *A61K 31/785* | (2006.01) |
| *A61K 31/66* | (2006.01) |

(52) U.S. Cl.
CPC .......... *A61K 31/661* (2013.01); *A61K 9/0048* (2013.01); *A61K 9/0053* (2013.01); *A61K 31/155* (2013.01); *A61K 31/785* (2013.01); *A61P 33/04* (2018.01); *A61K 31/66* (2013.01)

(58) Field of Classification Search
CPC .................................................. A61K 31/66
USPC .......................................................... 514/77
See application file for complete search history.

(56) References Cited

U.S. PATENT DOCUMENTS 7,887,817 B2   2/2011   Engel

FOREIGN PATENT DOCUMENTS

| WO | 2013135571 A1 | 9/2013 | |
|---|---|---|---|
| WO | WO-2016182032 A1 * | 11/2016 | ........... A61K 31/506 |

OTHER PUBLICATIONS

Mrva et al., "Weak Cytotoxic Activity of Miltefosine Against Clinical Isolates Acanthamoeba spp.", Journal of Parasitology, vol. 97, No. 3, pp. 538-540 (2011).*

(Continued)

*Primary Examiner* — Kevin E Weddington
(74) *Attorney, Agent, or Firm* — Dentons Cohen & Grigsby P.C.

(57) ABSTRACT

Methods of treating infections caused by free-living *amoeba* are disclosed. The methods generally include systemic administration of an effective amount of miltefosine, such as an oral or intravenous formulation, and optionally local administration of an effective amount of miltefosine, such as a topical formulation of miltefosine. The methods may further include administration of one or more secondary agents. Exemplary secondary agents include steroids, polyhexamethylene biguanide (PHMB), chlorhexidine, propamidine isethionate, dibromopropamidine isethionate, neomycin, paromomycin, polymyxin B, clotrimazole, ketoconazole, miconazole, and itraconazole. The methods may be used to treat patients with infections caused by a free-living *amoeba* such as *Naegleria fowleri, Balamuthia mandrillaris, Sappinia diploidea*, and *Acanthamoeba* species. Exemplary infections include *Acanthamoeba keratitis*, granulomatous amoebic encephalitis, cutaneous acanthamoebiasis, primary amoebic meningoencephalitis, *Sappinia* amoebic encephalitis, or a disseminated disease associated with a free-living *amoeba*.

22 Claims, No Drawings

(56) References Cited

OTHER PUBLICATIONS

English Translation for WO 2016/182032 A1 Oki et al.*

Seal, DV, Acanthamoeba keratitis update—incidence, molecular epidemiology and new drugs for treatment, Eye, vol. 17, p. 893-905, 2003.

Franzco, James McKelvie et al., The rising tide of Acanthamoeba keratitis in Auckland, New Zealand: a 7-year review of presentation, diagnosis and outcomes (2009-2016), Clinical and Experimental Opthalmology, vol. 46, p. 600-607, 2018.

Arita, Reiko et al., Development of Definitive and Reliable Grading Scales for Meibomian Gland Dysfunction, American Journal of Ophthalmology, p. 125-137, 2016.

Sifi SpA, Polyhexamethylene Biguanide (PHMB) Ophthalmic Solution in Subjects Affected by Acanthamoeba Keratitis, U.S. National Library of Medicine, Sep. 2017.

Rios-Marco, Pablo et al., Alkylphospholipids: An update on molecular mechanisms and clinical relevance, Biochimica et Biophysica Acta, vol. 1859, p. 1657-1667, 2017.

Polat, Zubeyda Akin et al., Efficacy of miltefosine for topical treatment of Acanthamoeba keratitis in Syrian hamsters, Parasitology Research, Jul. 2011.

Barisani-Asenbauer T., et al., Successful Management of Recurrent Acanthamoeva Keratitis Using Topical and Systemic Niltefosine, Acta Opthalmologia 2012, vol. 90, Issue S249, abstract.

Castro, MDM, et al., "Pharmacokinetics of Miltefosine in Children and Adults with Cutaneous Leishmaniasis," Antimicrobial Agents and Chemotherapy 2016, vol. 61, e021198-16.

Polat, ZA, et al., "Miltefosine and Polyhexamethylene Biguanide: A New Drug Combination for the Treatment of Acanthamoeva Keratitis," Clin Exp Ophthalmol 2014, vol. 42, No. 2, p. 151-158, abstract.

McClellan, K., et al., "Acanthamoebic Keratitis Diagnosed by Paracentesis and Biopsy and Treated with Proamidine," British Journal of Ophthalmology 1987, vol. 71, p. 734-736, abstract.

Ferrari, G., et al., "Double-Biguanide Therapy for Resistant Acanthamoeba Keratitis," Case Rep Ophthalmol 2011, vol. 2, p. 338-342.

* cited by examiner

TREATMENTS FOR FREE-LIVING AMOEBIC INFECTIONS

CROSS REFERENCE TO RELATED APPLICATIONS

The present application claims the benefit under 35 U.S.C. § 119(e) of prior U.S. Provisional Application No. 62/735,338 filed Sep. 24, 2018, the entire content of which is hereby incorporated by reference.

FIELD OF THE INVENTION

The present invention relates to methods for treating a subject having a free-living amoebic infection using systemic and/or local administration of miltefosine alone or in combination with a secondary agent.

BACKGROUND OF THE INVENTION

Free-living *amoebae* are able to exist as free-living organisms in nature and only occasionally invade a host and live as parasites within the host's tissue. While there are many varieties of free-living *amoeba*, only four genera (*Acanthamoeba, Balamuthia, Naegleria*, and *Sappinia*) have been associated with rare but devastating human disease. Because of this rarity, most published literature on amoebic infections consists of case reports, and a lack of established success in treatment regimens means there is no single, proven, evidence-based treatment that carries a high probability of cure.

*Acanthamoeba* and *Balamuthia* species are opportunistic pathogens causing infections of the CNS, lungs, sinuses and skin, mostly in immunocompromised humans. For example, *Acanthamoeba* species and *Balamuthia mandrillaris* most often cause subacute or chronic granulomatous amoebic encephalitis (GAE), usually in immunocompromised patients, and *Acanthamoeba* species can cause granulomatous skin lesions, amoebic keratitis and corneal ulcers following corneal trauma or in association with contact lenses. *Naegleria fowleri* lives in freshwater habitats, feeding on bacteria. It can (rarely) infect humans by entering the nose during water-related activities. Once in the nose, the *amoeba* travels to the brain and causes a severe brain infection called primary meningoencephalitis (PAM), which is usually fatal. Finally, *Sappinia diploidea* has been identified as a rare cause of amoebic encephalitis As mentioned, *Acanthamoeba* species can cause *Acanthamoeba keratitis*, which is a vision-threatening corneal infection. It is often characterized by pain out of proportion to clinical findings and the late appearance of a stromal ring shaped infiltrate. *Acanthamoeba keratitis* primarily affects otherwise healthy people, the majority of whom wear contact lenses; In the United States, an estimated 85% of cases occur in contact lens wearers. Recent estimates for incidence of the disease range from 1 to 2 cases per million in the United States to approximately one in every 30,000 contact lens users in Europe (Seal, D. V. *Acanthamoeba keratitis update—incidence, molecular epidemiology and new drugs for treatment*. Eye (2003) 17:893-905). While relatively rare, before 1996 every eyeball infected with *Acanthamoeba keratitis* in the United States was eventually lost to the infection. Since then, a multitude of drugs have been used to treat the infection, including antibiotics, antifungals, steroids, and the like. Moreover, the importance of *Acanthamoeba* as a corneal pathogen increased after a nationwide outbreak of *Acanthamoeba keratitis* was identified in 2003.

*Acanthamoeba* likely invade the cornea through a physical opening, such as a minor abrasion, in the corneal epithelium. Contact lens wear may facilitate direct inoculation of *Acanthamoeba* into the eye and promote infection through mechanical or hypoxic trauma to the cornea. Upon binding to mannose glycoproteins of the corneal epithelium, *Acanthamoeba* secretes proteins cytolytic to the epithelium as well as proteases that facilitate further penetration. IgA antibodies normally protect corneal epithelial cells from *Acanthamoeba* infection, however, certain *Acanthamoeba* species are capable of producing proteases that lead to antibody degradation. (McKelvie J, et al., *The rising tide of Acanthamoeba keratitis in Auckland, New Zealand: a 7-year review of presentation, diagnosis and outcomes*. Clin Exp Ophthalmol. (2018)).

Because the timing of exposure to *Acanthamoeba* is difficult to assess, and because the time required to establish infection is highly dependent on the size of the inoculum, the incubation period for *Acanthamoeba keratitis* is difficult to determine, but is thought to range from several days to several weeks. As such, the ideal anti-amoebic regimen for *Acanthameoba keratitis* is unclear.

Moreover, a recent Cochrane review concluded that there was insufficient evidence to compare the relative effectiveness and safety of different medications for *Acanthamoeba keratitis*. (Arita, R., et al., *Development of Definitive and Reliable Grading Scales for Meibomian Gland Dysfunction*. Am J Ophthalmol. (2016) 169:125-137). Most recent case series have reported treatment with multiple agents, which usually included a topical biguanide and diamidine, and occasionally an oral azole.

Combination therapy may be more effective than monotherapy in some cases, as suggested by a report of patients successfully treated with combination therapy after failing biguanide monotherapy. Theoretically, combining agents with different mechanisms of action offers several potential advantages: broader antimicrobial coverage, less de novo resistance, and possible synergy. However, additional topical agents could also cause epithelial toxicity and reduce adherence. Moreover, it is not clear that combination therapy is more effective, as most case series reporting biguanide monotherapy have shown favorable outcomes with this single-agent regimen. More information will soon be available from a randomized trial that compares polyhexamethylene biguanide (PHMB) monotherapy versus combination therapy with PHMB and propamidine (clinicaltrials.gov # NCT03274895: *Polyhexamethylene Biguanide (PHMB) Ophthalmic Solution in Subjects Affected by Acanthamoeba Keratitis*), though much remains unknown about how to manage *Acanthamoeba keratitis*.

There are two stages in the life cycle of most free-living *amoeba*: an active feeding stage, i.e., trophozoites, and a dormant cyst stage. The cysts are resistant to chlorination and antibiotics, and have thus far been very hard to treat. Trophozoites, which are also very hard to treat, feed on bacteria, yeast, and algae. However, both trophozoites and cysts can retain viable bacteria and may serve as reservoirs for bacteria with human pathogenic potential.

As such, optimal strategies for the treatment of amoebic infections such as *Acanthamoeba keratitis* are unclear and failures rates are high. Prolonged therapy is the general rule, since *Acanthamoeba* cysts are difficult to eradicate, and can cause disease recurrence if therapy is discontinued too early. The use of topical corticosteroids is controversial; some have advocated concomitant topical corticosteroids for ocular pain and inflammation, but many clinicians are hesitant to use corticosteroids since they have been shown to promote growth of *Acanthamoebae*, or may aid in converting the *Acanthamoebae* trophozoites to the cyst form, thereby lengthening the course of the disease. Although there have been many case series documenting the role of different agents for *Acanthamoeba keratitis*, there has been only one randomized controlled trial for *Acanthamoeba keratitis*. This trial compared two biguanide antiseptic agents, chlorhexidine and polyhexamethylene biguanide, and was unable to find a difference. Thus, the evidence base for treatment of *Acanthamoeba keratitis* is extremely weak.

Accordingly, new methods for treating free-living amoebic infections are desired and an object of the presently disclosed invention.

SUMMARY OF THE INVENTION

The present invention is based on the discovery that administration of miltefosine (2-[[(hexadecyloxy)hydroxyphosphenyl]oxy]-N,N,Ntrimethylethylammonium inner salt, also known as hexadecylphosphocholine) alone or in combination with a second agent, provides an effective treatment for free-living *amoeba* infections such as those caused by *Naegleria fowleri, Balamuthia mandrillaris, Sappinia diploidea,* and *Acanthamoeba* species, in both the free-living trophozoite and cyst forms.

Accordingly, the presently disclosed invention is related to treatment methods for infections caused by free-living *amoeba*. The methods generally comprise administration of an effective amount of miltefosine. The miltefosine may be provided systemically, such as intravenously or by an oral formulation (e.g., pill, capsule, iv fluid, or liquid) that may be ingested by a patient or administered to a patient undergoing treatment, and optionally may also be provided locally, such as a topical formulation applied to a site of infection (e.g., eye-drop, liquid, or cream/ointment).

According to certain aspects of the presently disclosed invention, administration of the miltefosine may be continued on a daily basis (from 1-8 times per day) for a period of time from at least one month up to at least six to twelve months.

According to certain aspects of the presently disclosed invention, the methods may be used to treat patients with infections caused by a free-living *amoeba* such as *Naegleria fowleri, Balamuthia mandrillaris, Sappinia diploidea,* and *Acanthamoeba* species. Exemplary *Acanthamoeba* species include any of the strains *A. castellanii, A. commandoni, A. culbertsoni, A. divionensisi, A. echinulata, A. griffin, A. hatchetti, A. healyi, A. jacobsi, A. lenticulata, A. lugdunensis, A. mauritaniensis, A. palestinensis, A. pearcei, A. polyphaga, A. pustulosaj, A. quina, A. rhysodes, A. royreba, A. stevensoni, A. triangularis,* and *A. tubiashi.*

According to certain aspects, the infection(s) treated by the methods of the presently disclosed invention may be an amoebic disease such as *Acanthamoeba keratitis*, granulomatous amoebic encephalitis, cutaneous acanthamoebiasis, primary amoebic meningoencephalitis, *Sappinia* amoebic encephalitis, or a disseminated disease associated with a free-living *amoeba*.

According to certain aspects of the presently disclosed invention, the methods may further comprise administration of a second agent, such as an antifungal, antiseptic, antibiotic, antiparasitic, or steroidal. Exemplary second agents include polyhexamethylene biguanide (PHMB), chlorhexidine, propamidine isethionate, dibromopropamidine isethionate, neomycin, paromomycin, polymyxin B, clotrimazole, ketoconazole, miconazole, itraconazole, vorconizole, etc. The secondary agent may be provided as an intravenous formulation, oral formulation (e.g., liquid, liquigel, tablet), or a topical or local formulation (e.g., eye drop, cream, ointment).

According to certain aspects of the presently disclosed invention, the systemically provided miltefosine may be administered at a first dose for a first time period, and at a second dose for a second time period. The second dose may be lower than the first dose. The time period of the second dose, however, may be longer than the time period of the first dose.

For example, the first dose may include a dose of 10 milligrams/day (i.e., 10 mg/day) to 200 mg/day, and the second dose may include a dose of 5 mg/day to 150 mg/day. Alternatively, the first dose may include a dose of 1 mg/kg/day to 10 mg/kg/day, and the second dose may include a dose of 0.5 mg/kg/day to 5 mg/kg/day. The first time period may be from at least one week to at least four weeks, and the second time period may be from at least two weeks to at least twelve months. The first and second doses may be administered one, two, three or more times per day as portions of the daily dose. For example, the portions of the daily dose may be equal portions.

According to certain aspects of the presently disclosed invention, the locally provided miltefosine may be administered hourly or daily during the first time period, and less frequently in the second time period (e.g., first and second time periods of the systemically provided miltefosine). According to certain aspects of the presently disclosed invention, the locally provided miltefosine may be a topical or local formulation comprising 5 μM to 2500 μM miltefosine, or may be a topical or local formulation configured to provide 0.05 μM to 500 μM miltefosine in the blood or 0.1 μM to 50 μmiltefosine in the cerebral spinal fluid (CSF) or tears of a patient being treated.

The objects of the present invention will be realized and attained by means of the combinations specifically outlined in the appended claims. The foregoing general description and the following detailed description and examples of this invention are provided to illustrate various aspects of the present invention, and by no means are to be viewed as limiting any of the described embodiments.

Definitions and Abbreviations

Throughout this description and in the appended claims, use of the singular includes the plural and plural encompasses singular, unless specifically stated otherwise. For example, although reference is made herein to "an" infection, "a" composition, or "the" pharmaceutical carrier, one or more of any of these components and/or any other components described herein may be used.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a method comprising administering a therapeutically effective amount of miltefosine with or without PHMB, a method "consisting essentially of" or "consisting of" administering the miltefosine with or without the PHMB is also within the present scope. In this context, "consisting essentially of" means that any additional components will not materially affect the efficacy of the method.

Moreover, other than in the examples, or where otherwise indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements. When ranges are given, any endpoints of those ranges and/or numbers within those ranges can be combined within the scope of the present invention.

"Synergistic combinations," as used herein, are combinations of monotherapies that may provide a therapeutic effect that is comparable to the effectiveness of a monotherapy, while reducing adverse side effects of the monotherapy, e.g. damage to epithelial tissues, epithelial toxicity, irritation of targeted tissues, and other clinical indicia. Alternatively, synergistic combinations may provide for an improved therapeutic effectiveness, which may be measured by a reduction in the total *amoeba* number (i.e., trophozoites, cysts, and/or other forms) or a length of time of the *amoeba* infection, or an improvement in other indicators of patient health. As example, for an *Acanthamoeba* infection that has caused *Acanthamoeba keratitis*, other indicators of patient health may include a reduction or disappearance of any of a corneal epithelial irregularity, an epithelial ulcer, an stromal infiltrate, a stromal ulcer, a radial keratoneuritis, a keratomalacia, a limbitis, perineuritis, a corneal microcysts, a punctate keratopathy, a bullous keratopathy, a disciform stromal keratitis, pseudodendritic keratitis, an anterior uveitis, a granulomatous stromal reaction, a stromal ring infiltrate formation, a conjunctivitis, a *keratitis*, a mucopurulent ocular discharge, an intermittent blepharospasm, a moderate conjunctivitis, an axial corneal edema, a multifocal linear anterior stromal leukocyte infiltration, a superficial corneal ulceration, a blepharitis, scleritis, a cataract, a chorioretinitis, or a corneal stromal abscess. Synergistic combinations of the present invention may combine a therapeutically effective amount of miltefosine with a therapeutically effective amount of a second agent.

"Pharmaceutically acceptable salt" refers to acid addition salts of basic compounds, e.g., those compounds including a basic amino group, and to basic salts of acidic compounds, e.g., those compounds including a carboxyl group, and to amphoteric salts of compounds that include both an acidic and a basic moiety, such that these salts are suitable for administration in vivo, preferably to humans. Various organic and inorganic acids may be used for forming acid addition salts. Pharmaceutically acceptable salts are derived from a variety of organic and inorganic counter ions well known in the art. Pharmaceutically acceptable salts include, when the molecule contains a basic functionality, by way of example only, hydrochloride, hydrobromide, tartrate, mesylate, acetate, maleate, oxalate and the like, and when the molecule contains an acidic functionality, by way of example only, sodium, potassium, calcium, magnesium, ammonium, tetraalkylammonium, N-methylmorpholinium, and the like. In one embodiment, the pharmaceutically acceptable salt of ezatiostat is ezatiostat hydrochloride.

"Treat" or "treatment" refers to therapeutic treatment wherein the object is to slow down (lessen) an undesired physiological change or disease, such as the development or spread of an infection, or to provide a beneficial or desired clinical outcome during treatment. Beneficial or desired clinical outcomes include alleviation of symptoms, diminishment of extent of infection, stabilization (i.e., not worsening) of the state of infection, delay or slowing of infection progression, and amelioration or palliation of the infection state. "Treatment" may also mean prolonging survival as compared to expected survival if a subject was not receiving treatment. Those in need of treatment include those subjects already presenting with the undesired physiological change or disease as well as those subjects prone to have the physiological change or disease (e.g., contact lens wearer with a current corneal abrasion).

The phrase "therapeutically effective amount" as used herein refers to an amount sufficient to provide treatment as defined herein, and may include an amount effective to inhibit protozoan growth associated with a protozoan infection or colonization, e.g., growth or colonization by a free-living *amoeba*. That is, reference to administration of the therapeutically effective amount of miltefosine according to the methods or compositions of the disclosed invention may be taken to refer to a therapeutic effect in which substantial protozoacidal or protozoastatic activity causes a substantial inhibition of protozoan infection. As such, a therapeutically effective amount may refer to a sufficient amount of the composition to provide the desired biological, therapeutic, and/or prophylactic result. The desired results include elimination of protozoan infection or colonization or reduction and/or alleviation of the signs, symptoms, or causes of an infection, or any other desired alteration of a biological system, such as indicated above with regard to synergistic combinations. In relation to a pharmaceutical or veterinary composition, effective amounts can be dosages that are recommended in the modulation of a diseased state or signs or symptoms thereof. Effective amounts may differ depending on the composition used and the route of administration employed. Effective amounts are routinely optimized taking into consideration various factors of a particular patient, such as age, weight, gender, etc. and the area affected by disease or disease causing protozoan.

"Patient" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. "Patient" and "subject" are used interchangeably herein.

"*Amoeba*" as used herein refers to a protozoan, preferably a pathogenic protozoan, isolated from the environment or from mammals (animals or human). *Amoeba* belonging to the *Acanthamoebidae* family encompass the genus *Acanthamoeba*, and members of this genus include amoeba species (spp.) such as, but not limited to, *A. castellanii, A. commandoni, A. culbertsoni, A. divionensisi, A. echinulata, A. griffin, A. hatchetti, A. healyi, A. jacobsi, A. lenticulata, A. lugdunensis, A. mauritaniensis, A. palestinensis, A. pearcei, A. polyphaga, A. pustulosaj, A. quina, A. rhysodes, A. royreba, A. stevensoni, A. triangularis*, and *A. tubiashi*. The term *amoeba*, as used herein, is also meant to include other disease causing *amoebae*, which may or may not belong to the *Acanthamoebidae* family, such as but not limited to, *Vahlkamfiidae, Entamoeba histolytica, Naegleria, Bala-*

*muthia, Hartmannella*, and *Sappinia* Additionally, the term *amoeba* also includes species that play hosts to bacterial pathogens, such as, by protecting them from disinfectants and allowing their multiplication within amoebal cysts. Furthermore, the term *amoeba* is also meant to include an as yet identified *amoeba* species, which preferably is a causative agent for ocular complications in mammals.

Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

DETAILED DESCRIPTION OF THE INVENTION

Small free-living *amoebas* belonging to the genera *Acanthamoeba, Balamuthia, Sappinia*, and *Naegleria* occur world-wide. They have been isolated from a variety of habitats including fresh water, thermal discharges of power plants, soil, sewage, and also from the nose and throats of patients with respiratory illness as well as healthy persons. Although the true incidence of human infections with these *amoebas* is not known, it is believed that as many as 200 cases of central nervous system infections due to these *amoebas* have occurred world-wide. A majority (144) of these cases have been due to *Naegleria fowleri* which causes an acute, fulminating disease, primary amoebic meningoencephalitis (PAM; brain eating *amoeba*). The remaining 56 cases have been reported as due either to *Acanthamoeba* or some other free-living *amoeba* which causes a subacute and/or chronic infection called granulomatous amoebic encephalitis (GAE). *Acanthamoeba*, in addition to causing GAE, also causes nonfatal, but nevertheless painful, vision-threatening infections of the human cornea, *Acanthamoeba keratitis*, including potential loss of the eye. Infections due to *Acanthamoeba* have also been reported in a variety of animals. These observations, together with the fact that *Acanthamoeba* species, *Naegleria fowleri*, and *Hartmannella* species can harbor pathogenic microorganisms such as *Legionella* and/or *Mycobacteria* indicate the public health importance of these *amoebas*.

*Acanthamoeba* Infections

Early diagnosis of infections caused by free living *amoeba* is often essential for effective treatment. For *Acanthamoeba keratitis*, several prescription eye medications are available for treatment. To date, the best treatment results have been obtained with topical administration of polyhexamethylene biguanide (PHMB), although this has not been successful in all cases. Treatment for advanced stages of *Acanthamoeba keratitis* may also include aggressive surgical interventions such as penetrating keratoplasty (full thickness corneal transplant). Skin infections caused by *Acanthamoeba*, which have not spread to the central nervous system, have also been successfully treated. Because this is a serious infection, and the people affected typically have weakened immune systems, early diagnosis offers the best chance of successfully curing the infection. Other *Acanthamoeba* infections include GAE, a serious infection of the brain and spinal cord that often strikes people with weakened immune systems, and disseminated disease. Drugs used in treating *Acanthamoeba keratitis* include cationic antiseptics, such as chlorhexidine and polyhexamethylene biguanide (PHMB); aromatic diamides, such as propamidine isethionate (Brolene®); and aminoglycoside antibiotics, such as neomycin.

*Balamuthia mandrillaris* Infections

Although there have been more than 200 cases of *Balamuthia* infection worldwide, few patients are known to have survived as a result of successful drug treatment. *Balamuthia mandrillaris* infections include GAE. Early diagnosis and treatment might increase the chances for survival. Drugs used in treating GAE caused by *Balamuthia* have included a combination of flucytosine, pentamidine, fluconazole, sulfadiazine and either azithromycin or clarithromycin.

*Naegleria fowleri* Infections

Although most cases of PAM caused by *Naegleria fowleri* infection in the United States have been fatal (139/143 diagnosed from 1962-2016), there have been several well-documented survivors in North America: one in California (1978), one in Arkansas (2013), one in Florida (2016), and one in Mexico (2003). It has been suggested that the California survivor's strain of *Naegleria fowleri* was less virulent, which contributed to the patient's recovery; In laboratory experiments, the strain did not cause damage to cells as rapidly as other strains. Multiple patients have received treatment similar to the California survivor, including amphotericin B, miconazole/fluconazole/ketoconazole, and/or rifampin, but only the patient in California has survived on this treatment regimen making it difficult to determine its efficacy. The Mexico, Arkansas, and Florida patients survived after treatment with miltefosine.

*Sappinia diploidea* Infections

*Sappinia diploidea* is a free-living *amoeba* found in soil contaminated with elk, bison, and cattle feces. This *amoeba* causes amoebic encephalitis, producing acute-onset nausea, vomiting, bifrontal headache, photophobia, and visual blurring. To date, treatment for such infection has included surgical removal of the tumor in the brain and a series of drugs provided after the surgery.

Systemic Miltefosine

The chemical name of miltefosine is 2-[[(hexadecyloxy)hydroxyphosphenyl]oxy]-N,N,N-trimethylethylammonium inner salt, also known as hexadecylphosphocholine, represented by the formula (I). The empirical formula is $C_{21}H_{46}NO_4P$, yielding a molecular weight of 407.57 g/mol. Miltefosine is a white powder that is freely soluble in water, 0.1 N HCl or NaOH, methanol, and ethanol.

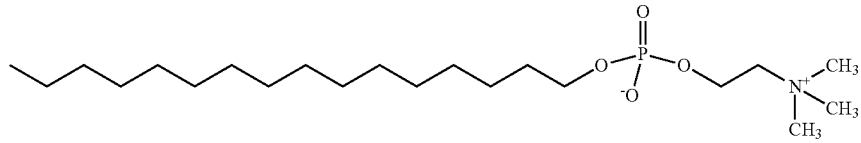

Formula I

Miltefosine belongs to the class of alkylphosphocholine drugs, which are phosphocholine esters of aliphatic long-chain alcohols. These alkylphosphocholine compounds are structurally related to the group of alkyl-lysophospholipids, which are synthetic analogues of lysophosphatidylcholines or lysolecithins, but lack their glycerol backbone. From a functional point of view, miltefosine is considered an inhibitor of Akt, otherwise known as protein kinase B (PKB). Akt/PKB is a crucial protein within the phosphatidylinositol 3-kinase/Akt/mammalian target of rapamycin (PI3K/Akt/mTOR) intracellular signaling pathway, which is involved in cell survival. (Rios-Marco, P, et al. *Alkylphosphohpids: An update on molecular mechanisms and clinical relevance*, Biochemica et Biopysica Acta (2017) vol. 1859, pg. 1657-67).

Miltefosine has shown *amoeba*-killing activity against free-living *amoebae*, including *Naegleria fowleri* in the laboratory, and *Balamuthia* and disseminated *Acanthamoeba* infections in patients. For example, as mentioned above, miltefosine was used successfully as an oral treatment for PAM. Moreover, a hamster model for *Acanthamoeba keratitis* showed that topical administration could bring a complete cure in 85% of the hamsters (160 µM, 28 days treatment; Polat, Z. A., et al., *Efficacy of miltefosine for topical treatment of Acanthamoeba keratitis in Syrian Hamsters*. Parasitol Res (2012) 110:515-20). However, it should be noted that the study only exposed the hamsters to the *Acanthamoeba* for 5 days, whereas in clinical settings a patient may have been exposed for weeks or months before the infection is detected, and/or treatment is initiated. Moreover, the presence of cysts in these hamsters was unknown, and may be the reason that reinfection rates were noted to be high. As such, no specific and successful treatment regime is currently known.

Free-living amoebic infections are especially hard to treat because the *amoeba* lives in both the metabolically active trophozoite state, i.e., "feeding" state, and the cyst state. Moreover, the longer a misdiagnosis goes on the greater the chance that the cysts will be out of the reach of typical topical treatments that (a) don't penetrate the various tissue layers successfully; (b) don't have a half-life long enough to survive the time for penetration to the cyst; or (c) don't have a mechanism of action that affects both the feeding and cyst forms.

Since miltefosine has been found to have a long half-life, and is known to cross the blood-brain barrier, the present inventor believed that either systemically, or systemically and locally (i.e., topically), the drug would be useful to kill *amoeba* in both the active feeding stage and the dormant cyst stage. Surprisingly, the present inventor has found systemic administration of miltefosine to be affective against both stages of the *amoeba*.

Miltefosine has previously been used to treat leishmaniasis, a rare tropical parasitic disease. Unlike treatment protocols for leishmaniasis, however, where dosing of 50 mg for 28 days was adequate, the present inventor found that longer treatment periods and different dosing schedules were needed to treat both the active feeding stage and the cyst stage of the *amoeba*.

Thus, the presently disclosed invention includes methods for treatment of free-living amoebic infections and diseases by providing miltefosine systemically, such as by administering miltefosine intravenously or as an oral formulation, for a longer period of time than known in the prior art. For example, the methods may include systemic administration of the miltefosine at a total daily dose of 10 milligrams/day (i.e., 10 mg/day) to 200 mg/day, such as 20 mg/day to 150 mg/day, or 50 mg/day to 150 mg/day. Administration may be in one or more doses spread throughout the day, such as one, two, three, or more doses, so that a total of all doses administered in one day provide the total daily dose (e.g., administering one, two, or three 50 mg tablets per day will provide a total daily dose of 50 mg, 100 mg, or 150 mg, respectively). Administration of the miltefosine may be for a period of at least four weeks, such as at least one month, or at least eight weeks, such as at least two months, or at least three months, or at least four months, or at least five months, or at least six months, or even at least twelve months, or more.

The methods may also include systemic administration of miltefosine at a total daily dose calculated based on patient weight, such as at a total daily dose of 0.5 mg/kg/day to 10 mg/kg/day, or 1 mg/kg/day to 8 mg/kg/day, or 1 mg/kg/day to 6 mg/kg/day, wherein the total daily dose may be administered in one, two, three or more doses throughout the day. As example, for oral administration to a 50 kg patient, the miltefosine may be administered as one, two, or three 50 mg tablets per day to provide a total daily dose of 1 mg/kg/day, 2 mg/kg/day, or 3 mg/kg/day, respectively. In another example, the miltefosine may be administered via intravenous infusion, wherein the dose may be administered continuously throughout the day to provide the total daily dose, or may be administered as boluses comprising a portion of the total daily dose infused over a shorter period of time, such as three doses infused over a one hour period wherein each dose comprises ⅓ of the total daily dose. While specific examples have been provided for illustrative purposes, various other portions and timings of intravenous boluses or oral doses are envisioned and within the scope of the present invention.

The methods of the presently disclosed invention may include systemic administration of the miltefosine according to more than one dosage regime, wherein each dosage regime includes the miltefosine administered at a total daily dose in one, two, three, or more doses or portions for a specific period of time. For example, the methods may include administration of the miltefosine according to a first dosage regime primarily focused on treatment of the trophozoites, followed by administration of the miltefosine according to a second dosage regime primarily focused on the cysts. The methods may include systemic administration of miltefosine according to a first dosage regime or "loading dose" comprising a first dose for a first time period of at least several days to one or more weeks or months, followed by systemic administration of miltefosine at a second dosage regime or "sustained dose" for a second time period of at least two or more weeks, such as at least one month to at least twelve months.

According to certain aspects of the presently disclosed invention, the first dosage regime may comprise the miltefosine administered systemically at a total daily dose of 10 mg/day to 200 mg/day, such as 20 mg/day to 150 mg/day, or 50 mg/day to 150 mg/day, in one, two, three, or more doses. For example, the miltefosine may be administered in 50 mg doses two or three times per day (i.e., providing the total daily dose of 100 mg/day or 150 mg/day, respectively) for a period of one week, two weeks, three weeks, four weeks or more.

After the miltefosine is administered according to the first dosage regime, it may be administered according to a second dosage regime, wherein the second dosage regime may comprise administering the miltefosine at a total daily dose of 5 mg/day to 150 mg/day for a time period of at least two or more weeks, such as at least four weeks, or at least one month, or at least eight weeks, such as at least two months, at least three months, at least four months, at least five months, at least six months, or even at least twelve months or more.

According to certain aspects of the presently disclosed invention, the second dosage regime may comprise administering the miltefosine at a total daily dose of 10 mg/day to 150 mg/day, such as 10 mg/day, or 20 mg/day, or 30 mg/day, or 40 mg/day, or 50 mg/day, or 60 mg/day, or 70 mg/day, or 80 mg/day, or 90 mg/day, or 100 mg/day, or 110 mg/day, or 120 mg/day, or 130 mg/day, or 140 mg/day, or 150 mg/day in one, two, three, or more doses per day. For example, the miltefosine may be administered in 10 mg doses two or three times per day (i.e., providing the total daily dose of 20 mg/day or 30 mg/day, respectively). Alternatively, the miltefosine may be administered in 50 mg doses two or three times per day (i.e., providing the total daily dose of 100 mg/day or 150 mg/day, respectively).

Alternatively, the first dose may include a dose of 1 mg/kg/day to 10 mg/kg/day, and the second dose may include a dose of 0.5 mg/kg/day to 5 mg/kg/day.

According to such a profile, which may include at least two dosage regimes, the methods may include administration of the miltefosine for four weeks or more, such as at least one month total, or up to about six months total, or even twelve months total or more to ensure killing of the amoeba in the cyst state.

As indicated above, the methods of the presently disclosed invention may be used to treat Acanthamoeba keratitis. Such infections have typically been hard to treat as the standard topical treatments generally don't permeate through the various tissue layers to the cysts of the amoeba. Using methods of the present invention, over eighty patients were treated with systemically administered miltefosine and preliminary feedback shows improvement over existing therapies. For example, more than a third of the patients with Acanthamoeba keratitis were treated with oral miltefosine for at least two months in order to effectively kill the cysts. The fact that an oral formulation of miltefosine was effective to treat Acanthamoeba keratitis and was able to kill both active feeding amoeba and cysts in the eyes was a surprising result. Previous treatment protocols for Acanthamoeba keratitis have only included topically applied agents such as biocides, and it is not clear from reported results whether cyst reduction was present at the end of these treatment protocols. Moreover, prior to 1996, every patient diagnosed with Acanthamoeba keratitis eventually lost the infected eye.

Local Miltefosine

According to certain aspects of the presently disclosed invention, the miltefosine may also be administered locally, such as via topical administration. For example, according to certain aspects, the methods of the presently disclosed invention may be used to treat Acanthamoeba keratitis, and the miltefosine may be administered both systemically as detailed above and locally to the eye.

Local administration of miltefosine may be via a topical formulation such as an ophthalmic composition (e.g., eyedrop, cream, ointment). As used herein, the term "ophthalmic composition" denotes a composition intended for application in the eye or intended for treating a medical device to be placed in contact with the eye, such as a contact lens. Ophthalmic compositions specifically include compositions for direct instillation in the eye, including eye drop solutions such as for treating dry eye, and contact lens treating solutions distilled directly in the eye such as for rewetting a contact lens while worn, and solid creams/ointments to be applied on a surface of the eye. Ophthalmic compositions also include compositions instilled indirectly in the eye, such as contact lens treating solutions for treating the contact lens prior to the lens being inserted on the eye, as well as contact lens multi-purpose solutions.

Local administration may occur concurrently with the systemic administration of miltefosine for all or a portion of the administration period of the latter. For example, the locally administered formulation (ophthalmic composition, topical cream/ointment, liquid drops or injection, etc.) comprising miltefosine may be administered concurrently with the systemic formulation of miltefosine during the first dosage regime, or a portion of the first dosage regime, of the latter. The locally administered formulation comprising miltefosine may be administered concurrently with the systemic formulation of miltefosine during the second dosage regime, or a portion of the second dosage regime, of the latter. The locally administered formulation comprising miltefosine may be administered concurrently with the systemic formulation of miltefosine during the first and second dosage regime of the latter. The locally administered formulation comprising miltefosine may be administered concurrently with the systemic formulation of miltefosine during the first dosage regime and only a portion of the second dosage regime of the latter. The locally administered formulation comprising miltefosine may be administered for a time period of at least four weeks, such as at least one month, or at least eight weeks, such as at least two months, or at least three, four, five, or even at least six months.

According to certain aspects, local administration of the miltefosine for treatment of such amoebic infections may occur only during the loading dose of the systemic formulation, or may be continued throughout both the loading and sustained doses of the systemic administration.

The local administration of miltefosine may be on a time schedule that is the same as the systemic administration of miltefosine, or may be on a different time schedule. For example, the local administration of miltefosine may be hourly, or every two hours, or every three hours during all or a portion of a day.

Miltefosine may be included in the local formulation at from 5 µM to 2500 µM, such as from 10 µM to 1000 µM, or from 10 µM to 500 µM, or even from 20 µM to 200 µM. The miltefosine may be included in a local formulation configured to provide 0.05 µM to 500 µM miltefosine in the blood or 0.1 µM to 50 µM miltefosine in the cerebral spinal fluid (CSF) or tears of a patient being treated.

According to certain other aspects, the methods of the presently disclosed invention may be used to treat cutaneous acanthamoebiasis or disseminated Acanthamoeba disease involving the skin, and the miltefosine may be administered systemically and locally, wherein the local administration may be via a topical liquid, cream/ointment, or powder formulation applied directly to the skin.

According to certain other aspects, the methods of the presently disclosed invention may be used to treat granulomatous amoebic encephalitis, primary amoebic meningoencephalitis, and/or Sappinia amoebic encephalitis. The miltefosine may be administered systemically and locally, wherein the local administration may be via a topical formulation such as a liquid that is applied directly to the brain, such as during surgery, or injected directly into the brain or surrounding regions, or the spinal column. Miltefosine has been found to kill amoeba, such as Acanthamoeba, in the brain within 48 to 72 hours. As such, according to certain aspects of the present invention, the systemic administration of miltefosine for the treatment of amoebic encephalitis or meningoencephalitis may be for a shorter time period than described for the treatment of other diseases or infections cause by amoeba (e.g., *Acanthamoeba keratitis*), such as one week, or two weeks, or three weeks. The local and systemic administration of the miltefosine may be concurrent, wherein the local administration may be for a shorter time period than the systemic administration.

Miltefosine Formulations

The miltefosine may be provided as a pharmaceutical composition, wherein the composition may be formulated by techniques known to the person skilled in the art, such as the techniques published in Remington's Pharmaceutical Sciences, $20^{th}$ Edition. The pharmaceutical compositions can be formulated as dosage forms for oral, parenteral, such as intramuscular, intravenous, subcutaneous, intradermal, intraarterial, nasal, or topical administration. Dosage forms for oral administration include coated and uncoated tablets, soft gelatin capsules (e.g., liquigels), hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for nasal administration can be administered via inhalation and insufflation, for example by a metered inhaler. Dosage forms for topical administration include creams, gels, ointments, salves, patches and transdermal delivery systems.

The miltefosine may be provided as a pharmaceutical composition, wherein the composition may be in the form of a single release formulation, a micronized formulation, or a controlled-release formulation that may include a degradable or non-degradable polymer, hydrogel, organogel, or other physical construct that modifies the release of the compound. It is understood that such formulations may include additional inactive ingredients that are added to provide desirable color, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

According to certain aspects of the presently disclosed invention, the miltefosine may be administered as an oral formulation that is a solid, such as a pill, capsule, or the like. As such, the formulations of the miltefosine of the invention may include inactive ingredients, such as colloidal silicon dioxide, microcrystalline cellulose, lactose monohydrate, talc, and magnesium stearate. For example, when formulated as a capsule, the shell may contain gelatin, titanium dioxide, ferric oxide, and purified water.

Miltefosine is freely soluble in aqueous solutions. Thus, according to certain aspects of the presently disclosed invention, the miltefosine may be administered as an oral formulation that is a liquid, such as included in a liquid capsule that may be swallowed, or as a formulation that a patient may drink. The miltefosine may be applied directly to body tissues such as skin or cornea. Alternatively, the miltefosine may be formulated as a solution that may be administered intravenously, such as formulated in a sterile saline solution.

According to certain aspects of the presently disclosed invention, the miltefosine may be administered locally and may comprise a topical composition formulated to include buffer components and salts (phosphate salts or other buffering salts, such as TRIS) in an amount effective in maintaining the pH of the solution within a physiologically acceptable range, preferably with a pH between 6 and 8. The topical composition may be formulation to include a preservative. For example, when the topical formulation is an ophthalmic composition, a preservative may be included. The term "preservative" or like terms denotes agents included in the compositions for the purpose of inhibiting the growth of microorganisms in the product, thereby helping to maintain sterility of the composition. Topical formulations may also include antimicrobial agents. The term "antimicrobial agent" denotes a specific active agent which provides antimicrobial efficacy.

Secondary Agents

The active stage of *amoeba*, trophozoites, feed on bacteria, yeast, and algae. Both trophozoites and cysts can retain viable bacteria and may serve as reservoirs for bacteria with human pathogenic potential. As such, according to certain aspects, methods of the presently disclosed invention include combining miltefosine with a second agent, such as one or more antimicrobial or antibacterial agents. Moreover, certain other drugs are known and used for treatment of amoebic infections, such as antifungal agents, antiparasitic agents, and antiseptic agents. These existing drugs used for amoebic infections may prove even more effective when combined with therapies including miltefosine. Moreover, treatments that combine systemic and optionally locally administered miltefosine with an additional agent(s) may enhance treatment of the both feeding and cyst stages of the infecting *amoeba*.

For example, drugs currently used for treatment of *Acanthamoeba keratitis* may expand the ability of the presently disclosed methods to address *Acanthamoeba keratitis* both on the surface of the eye as well as more penetrated *amoebas* in the feeding or cyst form.

Thus, according to certain aspects of the presently disclosed invention, the methods may include administration of at least one additional composition, such as at least one second composition that includes one or more second agent or drug. Exemplary second agents include one or more of a diamidine (e.g., dibromopropamidine isethionate (i.e., Brolene®), propamidine isethionate, hexamidine, pentamidine), biguanide (e.g., polyhexamethylene biguanide, chlorhexidine, alexidine), imidazole (e.g., clotrimazole, intraconazole, ketoconazole, vitraconazole), antifungal (e.g., caspofungin, natarnycin, miconazole, voriconazole, fluconazole, amphotericin B), aminoglycoside (e.g., neomycin), antiaminoglycoside (e.g., paromomycin), macrolide (e.g., rokitamycin, erythromycin), antibiotic (e.g., rifampin, metronidazole, moxifloxacin, vancomycin, tobramycin), plant extract (e.g., from *Rubus chamaemorus, Pueraria lobata, Solidago virgaurea* and *Solidago graminifolia, Pterocaulon polystachyum, Allium sativum, Thymus sipyleus*), atropine, N-chlorotaurine propolis, amidoamine myristamidopropyl dimethylamine or derivatives thereof or combinations thereof with other known or unknown compounds. Specific formulations and administration routes for specific secondary agents are may be those commonly known and used.

Topical steroids are frequently used to control corneal inflammation and uveitis or are administered after surgery to prevent corneal graft rejection. Thus, methods according to the presently disclosed invention, which include systemic and optional local administration of miltefosine, may also include administration of a steroid as a secondary agent, either orally or topically, for management of inflammation, such as inflammation of the eye found in *Acanthamoeba keratitis*. Studies have found, however, that treatment with steroids alone may increase pathogenicity of the trophozoites and cysts. The presently disclosed methods, which include miltefosine, may reduce this likelihood. Moreover, it is possible that treatment with steroids may reduce the autoimmune response that occurs after miltefosine treatment has been successful in killing the *amoeba*.

Accordingly, methods of the presently disclosed invention may include administration of a steroidal agent after the first month of treatment with the systemic miltefosine, or after the loading dose of miliefosine (i.e., systemic or local steroids may be administered during the sustained dose of the miltefosine). Methods of the presently disclosed invention may include administration of a steroidal agent concomitant with systemic and/or topical miltefosine to a patient after surgery, such as a corneal transplant or other surgery to treat or ameliorate an amoebic infection. The steroidal agent may be administered topically as an eye drop or ointment, or may be administered systemically, such as via an oral liquid, tablet, or intravenous administration. Specific steroids as well as formulations and administration routes (i.e., oral, intravenous, topical) may be those commonly known and used.

According to certain aspects of the presently disclosed invention, the second agent may comprise a biguanide such as hexamethylene biguanide and polymers thereof, i.e. polyhexamethylene biguanide (PHMB), chlorhexidine, alexidine, hexetidine, and the like. The hexamethylene biguanide represented by the formula (II) and a polymer thereof (n>1) are preferred.

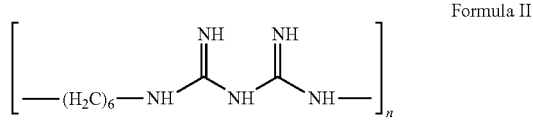

Formula II

According to certain aspects of the presently disclosed invention, when the second agent comprises a biguanide, the biguanide may be a mixture of a monomer having at least one biguanide group or a polymer thereof. A mixture containing a monomer and polymers having various degrees of polymerization, and a mixture containing polymers having various degrees of polymerization may also be collectively referred to as polybiguanide. For example, a mixture of a monomer of hexamethylene biguanide and a polymer thereof having various degrees of polymerization may also be collectively referred to as polyhexamethylene biguanide. When the mixture as mentioned above is used, an average degree of polymerization within the numerical range defined by n can be suitably used. For example, n may be from 1 to about 40, such as an average of about 10 to 13 so that an average molecular weight of the PHMB is generally 2,500 to 4,500. Additionally, the polybiguanide may be in the form of a salt, and may thus include a pharmaceutically acceptable salt.

The second agent may include a polybiguanide and a quaternary-ammonium compound, such as benzalkonium chloride and/or polyquaternium-1. The second agent may also contain one or more low molecular weight amino alcohols to further enhance the antimicrobial activity of the compositions. A preferred amino alcohol is 2-amino-2-methyl-propanol ("AMP").

The second agent may be administered concurrently with the systemic administration of miltefosine for all or a portion of the administration period thereof. For example, the second agent may be administered concurrently with the systemic administration of miltefosine during the first dosage regime, or a portion of the first dosage regime, of the latter. The second agent may be administered concurrently with the systemic administration of miltefosine during the first and second dosage regime of the latter. The second agent may be administered concurrently with the systemic administration of miltefosine during the first dosage regime and only a portion of the second dosage regime of the latter.

The second agent may be administered as a liquid, such as an ophthalmic composition (e.g., eye-drop) or a liquid composition to be ingested by the patient. The second agent may be administered as a solid ophthalmic composition (e.g., cream/ointment) formulated for application to the eye or as a solid tablet, capsule, or the like to be ingested by the patient.

The second agent may be formulation to include a preservative, such as when formulated as a liquid or a cream/ointment.

According to certain aspects of the presently disclosed invention, when the second agent includes a polybiguanide such as PHMB, wherein the PHMB may be formulation as eye-drops at concentrations of from 0.01% to 0.25% w/v, such as 0.02%, 0.04%, 0.06%, 0.08%, 0.1%, etc. According to certain aspects, the PHMB may be formulated as an eye-drop at 0.08% w/v.

According to certain aspects of the presently disclosed invention, the second agent may also include an additional agent, such as a diamidine. An exemplary diamidine includes dibromopropamidine isethionate (Brolene®), which may be included at 0.01% to 0.25% w/v, such as 0.1% w/v. According to certain aspects, the second agent may include an eye-drop comprising 0.01%-0.25% w/v PHMB and 0.01% to 0.15% w/v, dibromopropamidine isethionate, such as 0.02%-0.08% w/v PHMB and 0.01% to 0.10% w/v dibromopropamidine isethionate, or 0.02% w/v and 0.08% w/v dibromopropamidine isethionate. Dibromopropamidine isethionate is known to be quite toxic. However, in combination with the presently disclosed systemic and optional local administration of miltefosine, lower concentrations of the dibromopropamidine isethionate may be sufficient to provide effective treatment of amoebic infections. Thus, the dibromopropamidine isethionate may be included as a secondary agent in topical formulations at less than 0.08% w/v.

According to certain aspects of the presently disclosed invention, the second agent may be administered topically at least one time a day, such as two, three, or more times a day (e.g., every hour, every two hours, etc.). The dosing may be all day or may include a specific number of defined doses administered or applied throughout the day at defined time intervals, which may or may not include sleep hours. According to certain aspects, the second agent may be administered for at least one week, such as at least two, three, or four weeks or more. According to certain aspects, the second agent may be administered for at least one month, such as at least two, three, four, five, or six months, or more.

According to certain aspects of the presently disclosed invention, the second agent may be included in a liquid or solid formulation comprising both the second agent and the local formulation of miltefosine disclosed herein, wherein the liquid or solid formulation comprising both the second agent and the local formulation of miltefosine may be administered locally according to any of the methods disclosed herein for the local formulation of miltefosine.

According to certain aspects of the presently disclosed invention, the second agent may be included in a liquid or solid formulation comprising both the second agent and the systemic formulation of miltefosine disclosed herein, wherein the liquid or solid formulation comprising both the second agent and the systemic formulation of miltefosine may be administered systemically according to any of the methods disclosed herein for the systemic formulation of miltefosine.

According to certain aspects of the presently disclosed invention, the second agent may be included in an ophthalmic composition comprising both the second agent and the ophthalmic composition of miltdosine disclosed herein, wherein the ophthalmic composition comprising both the second agent and the miltefosine may be administered locally according to any of the methods disclosed herein for the ophthalmic composition of miltefosine.

All dosing schedules may include all hours of the day (i.e., 24 hours) or may exclude sleep hours (i.e., not administered during sleep hours).

Packs and Kits

The compositions of the presently disclosed invention may, if desired, be presented in a pack or dispenser device which may contain one or more unit dosage forms of the miltefosine. The pack may, for example, comprise metal or plastic foil, such as a blister pack. The dispenser device may, for example, comprise a bottle. The pack or dispenser device may be accompanied by instructions for administration, thus forming a kit.

According to certain aspects of the presently disclosed invention, the systemic formulation of miltefosine may be provided in a kit for carrying out the therapeutic methods of the invention. As such, the instructions may include directions for administration of an oral formulation of miltefosine, which may comprise directing the patient or caregiver to administer a unit dose of the systemic formulation at least two times per day (BID) for at least one month.

According to certain aspects of the presently disclosed invention, the systemic formulation of miltefosine and a second agent may be provided in a kit for carrying out the therapeutic methods of the invention. As such, the instructions may include directions for administration of the systemic formulation of miltefosine, which may comprise directing the patient or caregiver to administer a unit dose of the systemic formulation at least two times per day (BID) for at least one month, and administration of the second agent, which may comprise instructing the patient or caregiver to administer the second agent as at least two unit doses per day for at least one month.

According to certain aspects of the presently disclosed invention, the systemic formulation of miltefosine and the local formulation of miltefosine may be provided in a kit for carrying out the therapeutic methods of the invention. As such, the instructions may include directions for administration of an oral formulation of miltefosine and a topical formulation of miltefosine, which may comprise directing the patient or caregiver to administer a unit dose of the systemic and topical formulations at least two times per day (BID) for at least one month.

According to certain aspects of the presently disclosed invention, the systemic formulation of miltefosine, the local formulation of miltefosine, and one or more second agents may be provided in a kit for carrying out the therapeutic methods of the invention.

Such kits may include one or more containers having the various therapeutically effective amounts of the miltefosine and the second agent provided in pharmaceutically acceptable form. For example, the kits may comprise a solid dosage form of an oral formulation of miltefosine for systemic administration provided in a bottle or blister pack, and a liquid ophthalmic composition comprising one or more second agents and/or miltefosine in a pharmaceutically acceptable solution, e.g., in combination with sterile saline or a buffered solution, or other pharmaceutically acceptable sterile fluid. Alternatively, the ophthalmic composition comprising one or more second agents and/or miltefosine may be lyophilized or desiccated; in this instance, the kit optionally further comprises in a container a pharmaceutically acceptable solution (e.g., saline, etc.), preferably sterile, to reconstitute the complex to form the ophthalmic composition.

The kits may comprise a liquid dosage form of the oral formulation of miltefosine provided in a bottle (e.g., liquigel or drinkable liquid), a liquid ophthalmic composition comprising the second agent (e.g., eyedrop or ointment), and optionally another liquid ophthalmic composition comprising miltefosine. Either or both of the second agent and miltefosine may be lyophilized or desiccated, such that the kit may also comprise one or more containers a pharmaceutically acceptable solution to reconstitute the complex to form the ophthalmic composition.

The following aspects are disclosed in this application:

Aspect 1: A method for treating a subject having an infection caused by a free-living *amoeba*, the method comprising: administering a systemic formulation of hexadecylphosphocholine (miltefosine) for at least one week at a dose of 50 mg/day to 200 mg/day.

Aspect 2: The method according to aspect 1, wherein the systemic formulation is provided as an oral formulation.

Aspect 3: The method according to aspects 1 or 2, wherein the administering is continued on a daily basis for at least two weeks, or at least three weeks, or even at least four weeks, or at least one month, or at least eight weeks, or at least two months, or at least three months, or at least four months, or at least five months, or at least six months.

Aspect 4: The method according to any one of aspects 1 to 3, wherein the administering takes place two or three times per day.

Aspect 5: The method according to any one of aspects 1 to 4, wherein the systemic formulation of miltefosine is administered for a first time period at a first dose (loading dose) and for a second time period at a second dose (sustained dose).

Aspect 6: The method according to aspect 5, wherein the second time period is subsequent to the first time period.

Aspect 7: The method according to aspects 5 or 6, wherein the second dose comprises 50 mg/day to 150 mg/day miltefosine.

Aspect 8: The method according to any one of aspects 1 to 7, further including administering an effective amount of a local formulation of miltefosine.

Aspect 9: The method according to aspect 8, wherein the local formulation of miltefosine comprises a solution of 5 µM to 2500 µM miltefosine; or wherein the local formulation is configured to provide a concentration of 0.05 µM to 500 µM miltefosine in the subject's blood or 0.1 to 50 µM miltefosine in the subject's tears.

Aspect 10: The method according to any one of aspects 1 to 9, administering an effective amount of at least one second agent.

Aspect 11: The method according to aspect 10, wherein the at least one second agent comprises a topical or oral formulation of an antifungal, an antibiotic, an antiparasitic, an antiviral, a steroid, or any combination thereof.

Aspect 12: The method according to aspect 11, wherein the at least one second agent comprises a topical or oral formulation of polyhexamethylene biguanide (PHMB), chlorhexidine, propamidine isethionate, dibromopropamidine isethionate, neomycin, paromomycin, polymyxin B, clotrimazole, ketoconazole, miconazole, itraconazole, or a combination thereof.

Aspect 13: The method according to aspect 11, wherein the at least one second agent comprises PHMB, and the effective amount of the PHMB comprises 0.01% to 0.25% w/v.

Aspect 14: The method according to aspect 11, wherein the second agent comprises an ophthalmic formulation of polyhexamethylene biguanide (PHMB) and an ophthalmic formulation of dibromopropamidine isethionate Aspect 15: The method according to aspect 14, wherein the ophthalmic formulation of PHMB comprises 0.01% to 0.25% w/v PHMB and the ophthalmic formulation of dibromopropamidine isethionate comprises 0.01% to 0.15% w/v dibromopropamidine isethionate.

Aspect 16: The method according to aspect 11, wherein the at least one second agent comprises a steroid.

Aspect 17: The method according to aspect 16, wherein the steroid and systemic formulation of miltefosine are administered simultaneously but the steroid administration is started at least one week after the systemic formulation of miltefosine administration is started, such as at least two weeks, or at least three weeks, or at least four weeks after.

Aspect 18: The method according to aspect 16, wherein the systemic formulation of miltefosine is administered for a first time period at a first dose (loading dose) and for a second time period at a second dose (sustained dose), and wherein the steroid administration is during the sustained dose of the systemic miltefosine.

Aspect 19: The method according to any one of aspects 10 to 18, wherein the at least one second agent is administered for at least one week to at least six months.

Aspect 20: The method according to any one of aspects 1 to 19, wherein the infection caused by the free-living *amoeba* comprises *Acanthamoeba keratitis*, granulomatous amoebic encephalitis, cutaneous acanthamoebiasis, primary amoebic meningoencephalitis, *Sappinia* amoebic encephalitis, or a disseminated disease associated with a free-living *amoeba*.

Aspect 21: A kit comprising an oral formulation of miltefosine comprising 10 mg to 100 mg per unit dose; and instructions on an administration regime for the oral formulation, wherein the administration regime for the oral formulation of miltefosine comprise at least two unit doses per day for at least one month.

Aspect 22: The kit according to aspect 21, further comprising a topical formulation of polyhexamethylene biguanide (PHMB) comprising 0.01% to 0.25% w/v PHMB, wherein the instructions further include an administration regime for the topical formulation of PHMB.

Aspect 23: The kit according to aspects 21 or 22, further comprising a topical formulation of miltefosine, wherein the topical formulation of miltefosine comprises a solution of 5 µM to 2500 µM miltefosine, or wherein the topical formulation of miltefosine is configured to provide a concentration of 0.05 µM to 500 µM miltefosine in the blood, or wherein the topical formulation of miltefosine is configured to provide a concentration of 0.1 µM to 50 µM miltefosine in the cerebral spinal fluid (CSF) or tears of a patient being treated.

EXAMPLES

Several patients diagnosed with *Acanthamoeba keratitis* (AK) have been treated with systemic miltefosine, administered as 50 mg tablets BID or TID for one or more months. About ⅓ of those patients required administration of the systemic formulation of miltefosine for longer than one month. Since AK is commonly misdiagnosed, the stage of the disease when it is successfully identified varies greatly. As such, the stage at which treatment with the systemic miltefosine, or systemic and topical miltefosine, varies greatly and the administration duration for successful treatment was also found to vary greatly. For example, even with systemic administration of miltefosine, certain patients still required corneal transplants. A major advantage of the presently disclosed methods is that such patients could receive steroids after surgery while also receiving either or both of the systemic and topical formulations of miltefosine, and optional additional second agents. The present methods may reduce the increased pathogenicity of the trophozoites and cysts generally caused by steroid administration, thus allowing the steroid to suppress the autoimmune response after corneal transplant and increase success rates for the surgery.

Specific case study: a 32 year-old female patient presented to an ophthalmologist with dr eye, redness, and light sensitivity in her left eye. The patient was initially diagnosed with a moderate allergic reaction and a topical anti-inflammatory agent was prescribed (Lotemax®). Over the course of the next six weeks, the patient returned for re-evaluation nine additional times and was diagnosed with (a) conjunctivitis and newly prescribed an antibiotic ointment (Ciloxan®) in addition to the anti-inflammatory; (b) herpes simplex virus (HSV) and newly prescribed antiviral agents (Valtrex® and Zirgan®), followed by additional antibiotics (Cipro) and antivirals (Viroptic®); and (c) HSV with uveitis, and newly prescribed pain relieving drops (Durezol®) and a combination steroid antibiotic (Maxitrol®), while maintaining the antivirals (Valtrex® and Viroptic®).

Finally, on the 10$^{th}$ visit, a possible diagnosis for AK was established based on observation of a mild epithelial disruption, and the patient was sent for specialized testing (scrapping of the eye; confocal microscopy). After successful diagnosis, the patient was started on PHMB and chlorhexidine, and continued on Durezol®. Over the course of the next 26 weeks, PHMB and chlorhexidine were continued with addition of various other agents (steroids, antivirals, antibiotics). During that time, corneal thinning progressed to 90% and a corneal perforation was observed, leading to an emergency corneal transplant.

Within four weeks from surgery, the patient's eye started to show signs of deterioration, such as from an ongoing AK infection not cleared by the corneal transplant. The PHMB and chlorhexidine were continued. However, additional confocal microscopy testing showed that AK infection had returned and was progressing to the point of loss of vision and eventually the eye.

At this time, oral miltefosine administered at 50 mg TID was started and continued for just over a month. Medication was discontinued for one week, during which time the patient experienced renewed symptoms. These were likely from an immune response to the killed *amoeba* material The oral miltefosine was restarted in conjunction with oral steroids for a short course of treatment, after which the patient was maintained on oral miltefosine administered at 50 mg BID for an additional two months to clear the AK infection.

What is claimed is:

1. A method for treating a subject having an infection caused by a free-living *amoeba*, the method comprising:
   administering an oral formulation of hexadecylphosphocholine (miltefosine) at a first dosage of about 50 mg/day to about 200 mg/day for a first time period of at least one month; and
   administering an effective amount of at least one second agent, wherein the at least one second agent comprises a topical or oral formulation of an antifungal, an antibiotic, an antiviral, an antiparasitic, a steroid, or any combination thereof,
   wherein the infection caused by the free-living *amoeba* comprises *acanthamoeba keratitis*, granulomatous amoebic encephalitis, cutaneous acanthamoebiasis, primary amoebic meningoencephalitis, sappinia amoebic encephalitis, or a disseminated disease associated with a free-living *amoeba*.

2. The method of claim 1, wherein the at least one second agent comprises polyhexamethylene biguanide (PHMB), chlorhexidine, propamidine isethionate, dibromopropamidine isethionate, neomycin, paromomycin, polymyxin B, clotrimazole, ketoconazole, miconazole, itraconazole, or a combination thereof.

3. The method of claim 1, wherein the at least one second agent is an ophthalmic formulation comprising 0.01% to 0.25% w/v polyhexamethylene biguanide (PHMB) that is administered for at least one month, wherein the oral formulation of miltefosine is administered at least two times per day in evenly split doses equaling the first dosage, and the ophthalmic formulation of PHMB is administered at least two times per day.

4. The method of claim 2, further comprising:
   administering an oral formulation of hexadecylphosphocholine (miltefosine) at a second dosage of about 10 mg/day to about 150 mg/day for a second time period extending beyond the first time period, wherein the second time period is from at least one month to at least six months.

5. A method for treating a subject having an infection caused by a free-living *amoeba*, the method comprising:
   administering an oral formulation of hexadecylphosphocholine at a first dosage of about 50 mg/day to about 200 mg/day for a first time period of at least one month;
   administering an effective amount of at least one second agent during the first time period, wherein the at least one second agent comprises polyhexamethylene biguanide (PHMB), chlorhexidine, propamidine isethionate, dibromopropamidine isethionate, neomycin, paromomycin, polymyxin B, clotrimazole, ketoconazole, miconazole, itraconazole, or a combination thereof;
   administering an oral formulation of hexadecylphosphocholine at a second dosage of about 10 mg/day to about 150 mg/day for a second time period extending beyond the first time period, wherein the second time period is from at least one month to at least six months; and
   administering an effective amount of at least one second agent during at least a portion of the second time period, wherein the at least one second agent is a steroid,
   wherein the infection caused by the free-living *amoeba* comprises *acanthamoeba keratitis*, granulomatous amoebic encephalitis, cutaneous acanthamoebiasis, primary amoebic meningoencephalitis, sappinia amoebic encephalitis, or a disseminated disease associated with a free-living *amoeba*.

6. The method of claim 4, wherein the first dosage and the second dosage are each administered at least two times per day in evenly split doses.

7. A kit comprising:
   an oral formulation of miltefosine comprising 10 mg to 100 mg per unit dose;
   a topical formulation of polyhexamethylene biguanide (PHMB) comprising 0.01% to 0.25% w/v PHMB; and
   instructions on an administration regime for the oral formulation and the topical formulation, wherein the administration regime for the oral formulation of miltefosine comprise at least two unit doses per day for at least one month.

8. The kit of claim 6, further comprising a topical formulation of miltefosine, wherein the topical formulation of miltefosine comprises a solution of 5 µM and 2500 µM miltefosine, and wherein the topical formulation is configured to provide a concentration of 0.055 µM and 500 µM miltefosine in the blood or 0.1 µM to 50 µM miltefosine in the cerebral spinal fluid (CSF) or tears of a patient being treated.

9. A kit comprising:
   an oral formulation of miltefosine comprising 10 mg to 100 mg per unit dose;
   a topical or oral formulation of miconazole; and
   instructions on an administration regime for the miltefosine, and the miconazole, wherein the administration regime for the oral formulation of miltefosine comprise at least two unit doses per day for at least one month.

10. The kit of claim 9, further comprising a topical formulation of miltefosine, wherein the topical formulation of miltefosine comprises a solution of 5 µM and 2500 µM miltefosine, and wherein the topical formulation is configured to provide a concentration of 0.055 µM and 500 µM miltefosine in the blood or 0.1 µM to 50 µM miltefosine in the cerebral spinal fluid (CSF) or tears of a patient being treated.

11. The method of claim 1, wherein the at least one second agent comprises miconazole.

12. The method of claim 11, wherein the miconazole is administered for at least one month, wherein the oral formulation of miltefosine is administered at least two times per day in evenly split doses equaling the first dosage, and the miconazole is administered at least two times per day.

13. The method of claim 1, further comprising:
   administering an effective amount of a local formulation of miltefosine.

14. The method of claim 13, wherein the local formulation of miltefosine comprises a solution of 5 µM to 2500 µM miltefosine, wherein the local formulation is configured to provide a concentration of 0.05 µM to 500 µM miltefosine in the subject's blood or 0.1 µM to 50 µM miltefosine in the subject's tears.

15. The method of claim 1, wherein administering the oral formulation of miltefosine and the effective amount of at least one second agent is continued on a daily basis for at least eight weeks.

16. The method of claim 1, wherein the at least one second agent is administered for at least one week to at least six months.

17. The method of claim 1, wherein the at least one second agent comprises an ophthalmic formulation of PHMB comprising 0.01% to 0.25% w/v PHMB and an ophthalmic formulation of dibromopropamidine isethionate comprising 0.01% to 0.15% w/v dibromopropamidine isethionate.

18. The method of claim 1, further comprising:
administering an oral formulation of miltefosine at a second dosage of about 10 mg/day to about 150 mg/day for a second time period extending beyond the first time period, wherein the second time period is from at least one month to at least six months; and
wherein the at least one second agent further comprises a steroid administered during at least a portion of the second time period.

19. The kit of claim 7, further comprising a topical or oral formulation of a steroid, wherein the instructions on the administration regime further comprise instructions for administration of the steroid.

20. The kit of claim 9, further comprising a topical or oral formulation of a steroid, wherein the instructions on the administration regime further comprise instructions for administration of the steroid.

21. The method of claim 1, wherein the at least one second agent comprises a topical or oral formulation of a steroid, and wherein the steroid and the oral formulation of miltefosine are administered simultaneously but the steroid administration is started at least one week after the oral formulation of miltefosine administration is started.

22. A method for treating a subject having an infection caused by a free-living *amoeba*, the method comprising:
administering an oral formulation of hexadecylphosphocholine (miltefosine) at a dosage of about 50 mg/day to about 200 mg/day for a time period of at least four weeks;
administering an effective amount of at least one second agent, wherein the at least one second agent comprises a topical or oral formulation of polyhexamethylene biguanide (PHMB), chlorhexidine, propamidine isethionate, dibromopropamidine isethionate, neomycin, paromomycin, polymyxin B, clotrimazole, ketoconazole, miconazole, itraconazole, or a combination thereof; and
administering an affective amount of a topical or oral formulation of a steroid, wherein administration of the steroid is started at least one week after initiation of the administration of the oral formulation of miltefosine,
wherein the free-living *amoeba* is selected from the group consisting of *Naegleria fowleri, Balamuthia mandrillaris, Sappinia diploidea*, and *Acanthamoeba* species.

* * * * *